US00PP15047P2

(12) United States Plant Patent
Jernigan

(10) Patent No.: US PP15,047 P2
(45) Date of Patent: Jul. 27, 2004

(54) CANNA HYBRIDA PLANT NAMED 'MNIMAR'

(50) Latin Name: *Canna hybrida*
Varietal Denomination: MNImar

(75) Inventor: Brian James Jernigan, Dearing, GA (US)

(73) Assignee: McCorkle Nurseries, Inc., Dearing, GA (US)

( * ) Notice: Subject to any disclaimer, the term of this patent is extended or adjusted under 35 U.S.C. 154(b) by 10 days.

(21) Appl. No.: 10/715,606

(22) Filed: Nov. 17, 2003

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Jondle & Associates P.C.

(57) ABSTRACT

A new and distinct cultivar of *Canna hybrida* named MNImar characterized by the novelty of multiple inter-veinal striped yellow-green foliage with compact, large pink flowers that complement the foliage and shed quickly after they are spent, and dwarf growth habit. The combination of these characteristics on a single plant make MNImar a worthy new introduction well suited for the garden or container.

3 Drawing Sheets

Genus and species: *Canna hybrida.*
Variety denomination: 'MNImar'.

SUMMARY OF THE INVENTION

The present invention was selected as a sport from a group of divisions of the *Canna hybrida* 'Pink Sunburst' (unpatented) grown in a cultivated area due to its distinctively different foliage color having no rose coloration within the leaves as it's parent *Canna hybrida* 'Pink Sunburst' does. The invention is unlike any other variegated leafed Canna due to the combination of green/yellow foliage, pink flowers, and a dwarf growth habit. Bengal Tiger has similar foliage color, but is not dwarf, growing to six feet in one season and also does not have pink flowers, it has bright orange flowers by comparison.

ORIGIN AND ASEXUAL REPRODUCTION

Asexual reproduction of a Canna is preformed by the growth of rhizomes and separation of growing eyes from the mother plant. The new cultivar was divided and successfully propagated in July 2003 without any reversion or mutation of the new cultivar's characteristics at in Dearing, Ga. It has been found to retain its distinctive characteristics through successive propagations; and this novelty if firmly fixed.

The new cultivar is being grown in full sun in a pine bark sand media under normal nursery conditions, 5 gallon and 3 gallon containers.

DESCRIPTION OF PHOTOGRAPH

This new canna plant is illustrated by the accompanying photograph which shows blooms, buds, and foliage of the plant in full color, the colors shown being as true as can be reasonably obtained by conventional photographic procedures.

DESCRIPTION OF THE NEW CULTIVAR

Figure 1:
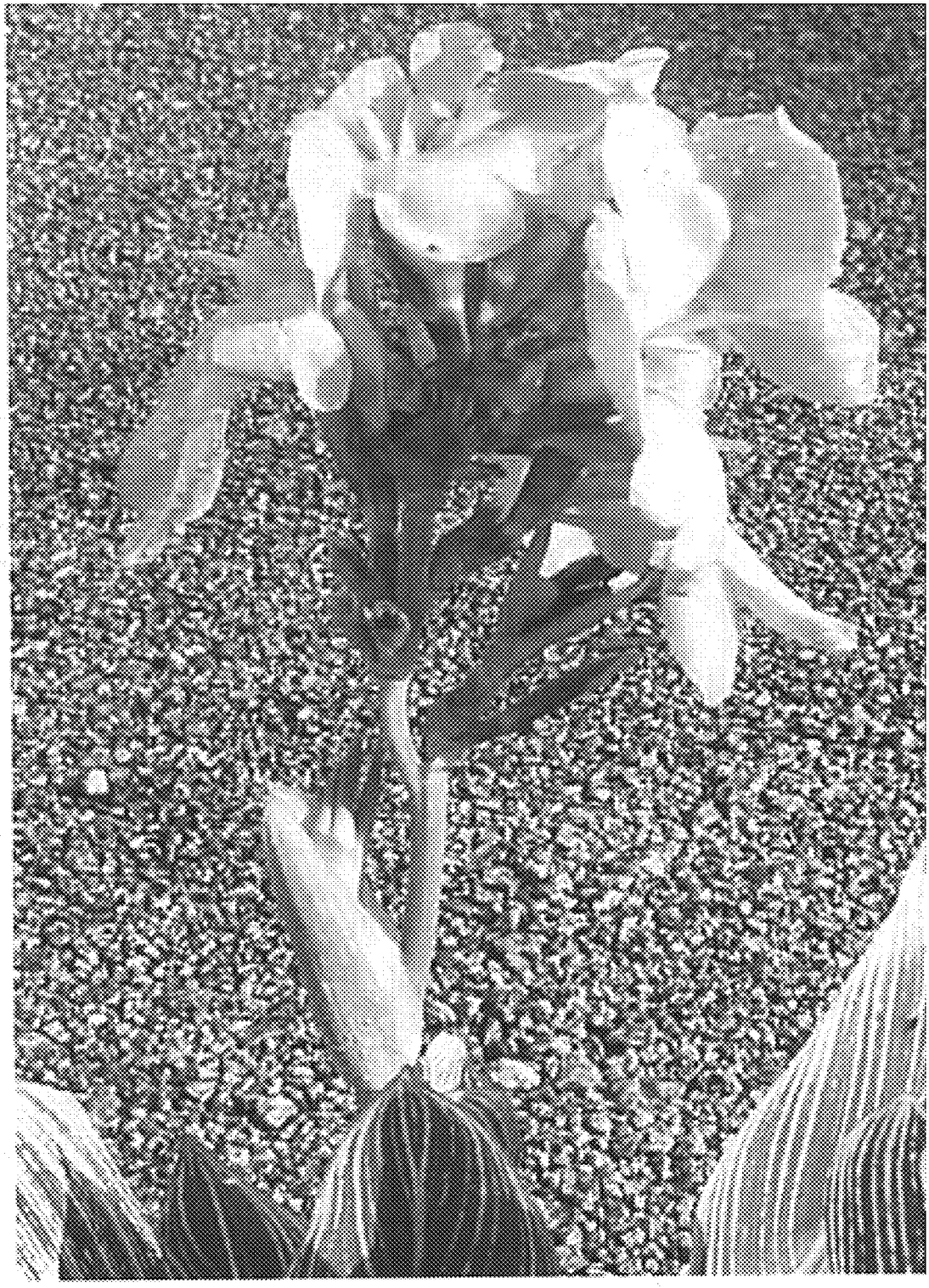
FIG. 1 is a close-up view of the plant showing the color of the petals.
Figure 2:
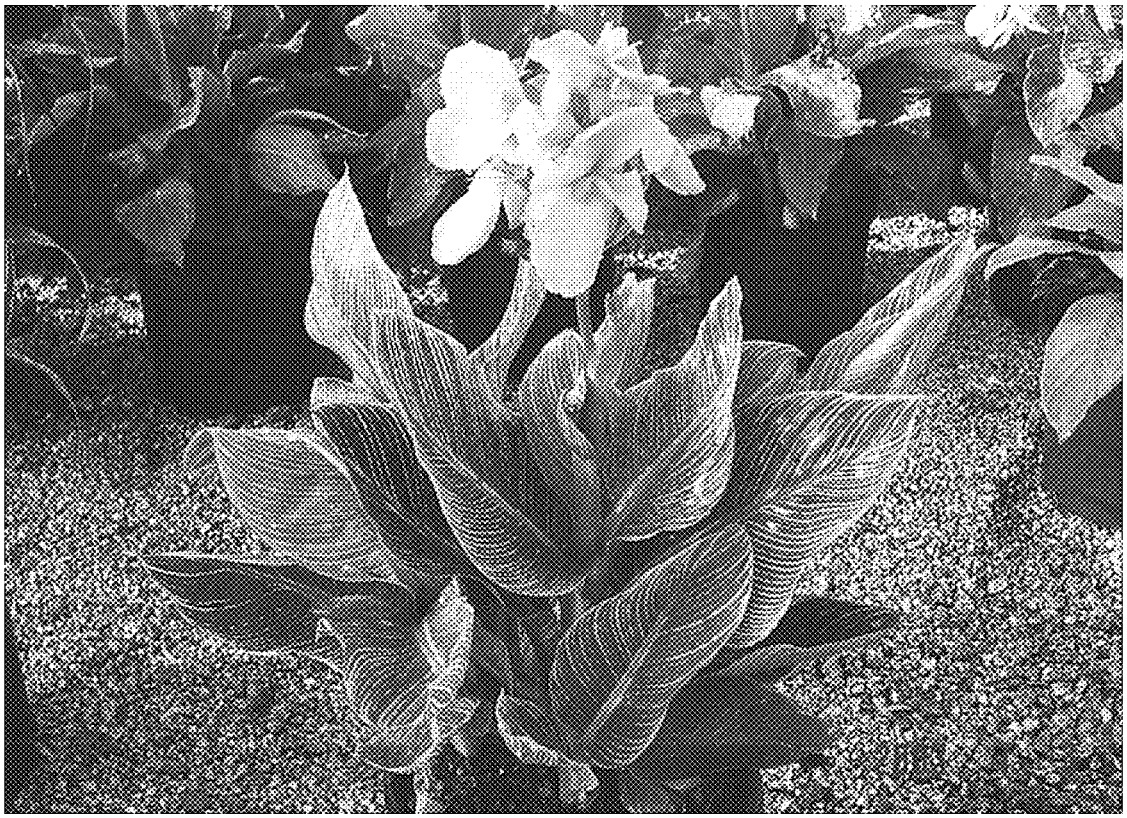
FIG. 2 is a view of the entire plant showing its form in pot culture when in full bloom.
Figure 3:
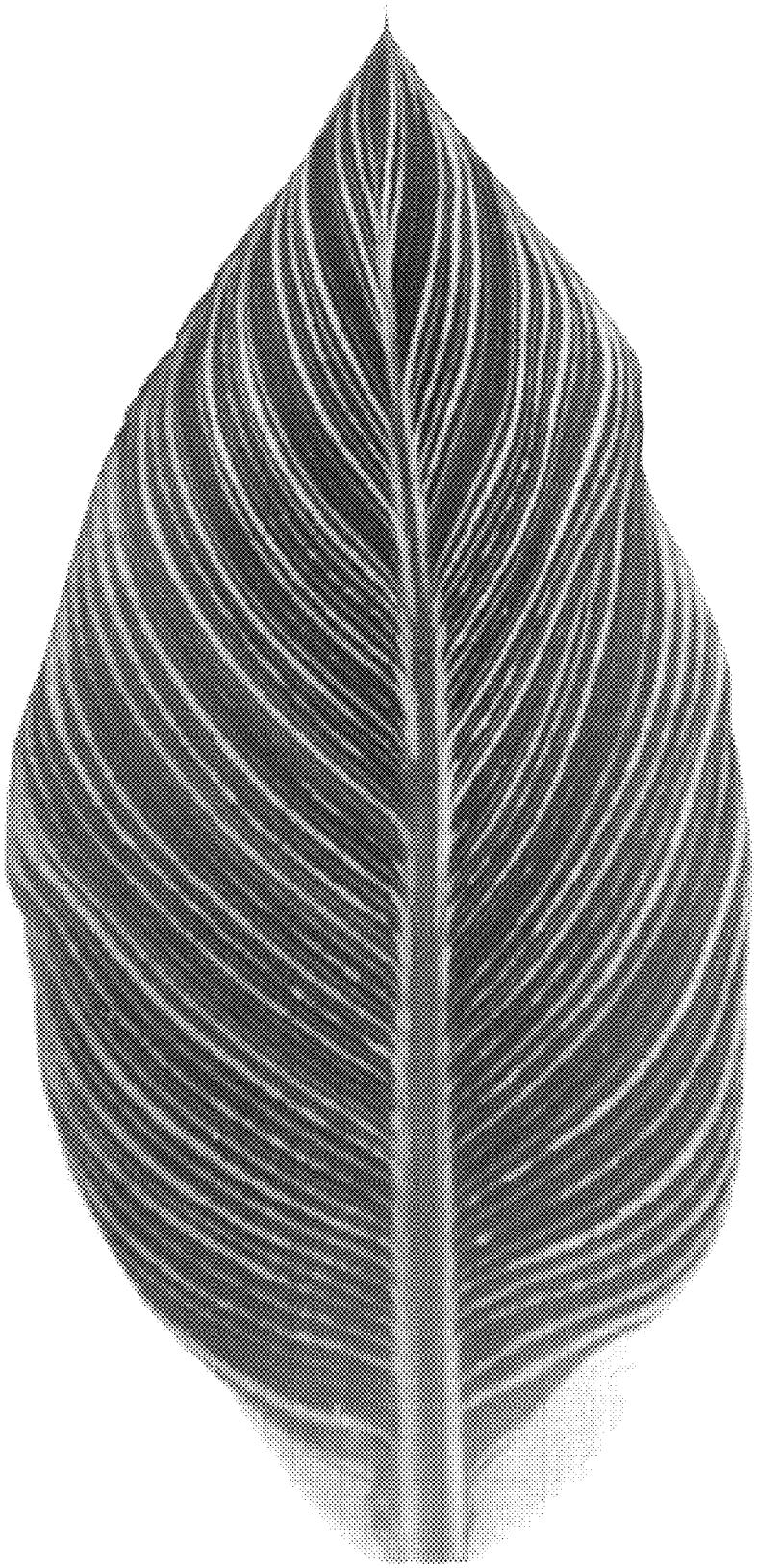
FIG. 3 is a close-up view showing the leaf color.

The following detailed descriptions set forth the distinctive characteristics of 'MNImar'. The data which defines these characteristics were collected from asexual reproductions carried out in Dearing, Ga. The plant history was taken on 3 month old fully mature and blooming plants in five and three gallon pots, under normal nursery conditions. Color references are primarily to The R.H.S. Colour Chart of The Royal Horticultural Society of London (R.H.S.).

DETAILED BOTANICAL DESCRIPTION

Classification:

*Botanical.*—*Canna hybrida.*

*Commercial.*—*Canna hybrida* named 'MNImar'.

*Habit.*—Forms a dense upright mass of stems topped by flowering panicles, slowly expanding in width by rhizomes beneath the soil surface.

*Height.*—A maximum height of 525 mm is achieved in the first growing season.

*Texture.*—The large 300 mm by 140 mm leaves give the plant a dense coarse texture in the landscape with clean smooth lines of the foliage.

The stems:

*Color.*—Ranges from lime green (RHS 145D) at soil level, to light green (RHS 145C) and (RHS 145B) shaded by the leaf petiole, to green (RHS 143C) exposed to the sun.

*Diameter.*—Ranges from 21.8 mm at the base to 11 mm at the flowering panicle.

*Shape.*—Stems are rounded, slightly oval in shape.

*Pith.*—Solid, lime green in color (RHS 149D).

*Internode length.*—Varies with area of the plant taken, the internode closest to ground level is 11 mm in length, the internode just below the flower panicle is 56 mm in length. The remaining internodes above ground are within the 11 to 56 mm inch range.

The leaves:

*Color.*—Leaves — from emergence to 30 days after unfolding to mature size exhibit three colors, a base color of green (RHS 139A), an irregular yellow (RHS 7A) variegation running parallel to the leaf veins from the midrib to the leaf margin that ranges from 1 to 2 mm in diameter with no pattern of occurrence denity, and a 2 mm rose (RHS 53A) margin on the outer edge of the leaf from the leaf tip to half way back to the petiole. b. Mature foliage 30 days or more in age exhibit two colors, a base color of green (RHS 139A) with the same irregular variegation that has faded to a cream (RHS 2D) color. There is no longer a different colored margin on the leaf. c. Midrib has strips of yellow (RHS 150C) and green (RHS 141D) running in irregular lines parallel to the midrib on the underside of the leaf. On the top side of the leaf, there is a thick green (RHS 139C) stripe in the center of the midrib running the length of the midrib that is surrounded by yellow (RHS 150C).

*Mature size.*—Average 300 mm in length and 140 mm in width.

*Shape.*—Ovate and broad elliptical with an entire margin and pinnate veination.

*Arrangement.*—Form an opposite alternate arrangement on the stem.

*Texture.*—Thick, leathery feel, with leaf ribs able to be felt on the leaf and with a distinct shine to it with what appears to be a high degree of waxiness.

The petiole:

*Length.*—Average 200 mm, shorter petioles are found on lower leaves (70 mm) with the longest petiole on the highest and largest leaf.

*Shape.*—Petioles form from a node and completely surround the stem opening to a curved shape at the leaf blade with a thick crescent shaped area at the back center of the curve.

*Color.*—The petiole color is a continuation of the markings on the leaf midrib. The petiole has strips of yellow (RHS 150C) and green (RHS 141D) running in irregular lines parallel from the base of the leaf to the stem. On the inside of the petiole, the side facing the stem, there is a thick green (RHS 139C) stripe in the center that runs the length of the petiole and is surrounded by yellow (RHS 150C).

*Diameter.*—The curve is 15 mm across.

The buds:

*Size.*—Average 28 mm length and 6 mm wide.

*Color.*—The color fades from a reddish (RHS 44A) at the visible tip to a yellow (RHS 1C) at the base.

*Shape.*—Lanceolate.

*Time range.*—Buds may be visible from mid May to Frost depending on growth stage of the plant.

The inflorescence:

*Type.*—Inflorescence a terminal raceme branching at the bracteate, forming secondary racemes. The flowers of the terminal raceme open first followed by the formation and flowering of secondary racemes. The flowers are born in pairs on short pedicels. Each flower or pair of flowers is subtended by a bract. Flowering from Early Summer to Frost.

*Size.*—A single flower raceme measures 100 mm by 80 mm wide and 100 mm high at first flowering.

*Color.*—Stem color is green (RHS 143C).

*Number of individual flowers per inflorescence.*—a. Each raceme averages 7 individual flowers. b. Each stem averages 3 racemes. c. Each inflorescence averages 21 individual flowers.

*Pedicel color.*—Green (RHS 143C).

*Pedicel length.*—Short pedicels 3 mm in length are at the base of each flower.

The flower:

*Petal size.*—Averages 52.25 mm in width and 80.25 mm in length united at the base, with three in each flower.

*Petal shape.*—Petals are narrow at the base becoming broad and rounded at the end in a spatulate shape.

*Petal margin.*—Solid margin around the petal.

*Petal texture.*—Soft, silky pliable texture.

*Petal color peak of bloom.*—Solid pink (RHS 49C) with darker pink (RHS 49A) veins lightly visible on both upper and lower sides.

*Sepal size.*—41 mm long by 15 mm wide.

*Sepal shape.*—Long narrow lance shaped rapping around the pedals.

*Sepal margin.*—Solid margin.

*Sepal texture.*—Smooth.

*Sepal color at peak of bloom.*—a. Upper surface: (RHS N34C). b. Lower surface: (RHS 19A) shaded by other plant parts.

The male reproductive structures:

*Stamens.*—1 per flower that is formed by a petaloid with a single anther on the upper surface.

*Anther size.*—10 mm long and 2 mm wide.

*Anter color.*—Tan (RHS 199C).

*Filament.*—Filament is fused into a petaloid 12 mm wide and 51 mm long; the petaloid is Pink (RHS 49C) with yellow (RHS 12C) spotting at the apex.

*Pollen color.*—Light tan (RHS 159C).

The female reproductive structures:

*Ovary shape.*—Three locular, verrucose, capsule.

*Ovary size.*—7 mm in width and 7 mm high.

*Ovary position.*—Inferior below petals, calyx, and sepals, visible beneath the flower.

*Ovary color.*—Green (RHS 142A).

*Stigma shape.*—Apex.

*Stigma color.*—Creamy orange (RHS 28C).

*Style length.*—50 mm by 5 mm.

*Style shape.*—Smooth flat and broad, slightly curving.

*Style color.*—Glossy yellow (RHS 12B).

The fruit:

*Type.*—A single verrucose capsule is formed per flower after flower senescence about 1 percent of the time under normal nursery conditions.

*Size.*—The Seed pod grows to 20 mm by 20 mm with three distinct compartments. The pod will expand further if seed is formed to encompass all of the seed, but usually it will shrivel and die.

*Color during ripening.*—The seed pod starts with a dark green (RHS 143C) and lightens to a slightly lighter green (RHS 144B) as it expands.

*Persistence.*—The Seed pod will only grow larger with seed present, generally it will shrivel and die on the plant, dropping afterward.

The seed:

*Shape.*—A smooth, rounded, oval seed is formed with a hard outer coating.

*Size.*—9 mm long and 7 mm in diameter.

*Color.*—Hard, shiny, dark brown (RHS 200A) coating.

*Germination capacity.*—Germination is not uniform and indeterminate.

I claim:

1. A new and distinct cultivar of Canna plant as shown and described herein.

* * * * *